United States Patent [19]

Ong et al.

[11] Patent Number: 5,334,715
[45] Date of Patent: Aug. 2, 1994

[54] 1-PIPERAZINYL-2-BUTENES AND -2-BUTYNES

[75] Inventors: Helen H. Ong, Whippany; Nicholas J. Hrib, Somerville, both of N.J.; Joseph Perez, Amherst, N.H.; John G. Jurcak, Somerset, N.J.

[73] Assignee: Hoechst-Roussel Pharmaceuticals Inc., Somerville, N.J.

[21] Appl. No.: 986,415

[22] Filed: Feb. 1, 1993

Related U.S. Application Data

[62] Division of Ser. No. 875,477, Apr. 29, 1992, Pat. No. 5,194,436, which is a division of Ser. No. 639,639, Jan. 10, 1991, Pat. No. 5,130,315.

[51] Int. Cl.$^5$ ............... C07D 295/00; C07D 403/00; C07D 413/00; C07D 401/00
[52] U.S. Cl. .................... 544/392; 544/230; 544/295; 544/362; 544/363; 544/364; 544/368; 544/369; 544/373; 544/376; 544/54
[58] Field of Search ............... 544/369, 295, 392, 363, 544/368, 376

[56] References Cited

U.S. PATENT DOCUMENTS

| | | | |
|---|---|---|---|
| 4,367,335 | 1/1983 | Temple et al. | 544/369 |
| 4,933,453 | 6/1990 | Hrib et al. | 544/369 |
| 5,034,392 | 7/1991 | Hrib | 544/369 |

FOREIGN PATENT DOCUMENTS 0196096 10/1986 European Pat. Off. .
63-10786 1/1988 Japan .
2177395H 1/1987 United Kingdom .

OTHER PUBLICATIONS

Y.-H. Wu, et al., Journal of Medicinal Chemistry, 12, 876 (1969) published in the U.S. and entitled "Psychosedative Agent, N-(4-Phenyl-1-piperazinylalkyl)-Substituted Cyclic Amides".

M. S. Gibson and R. W. Bradshaw, Angewandte Chemie, International Edition 7, 919 (1968) published in the U.S. and entitled "The Gabriel Synthesis of Primary Amines".

Y. Kojima, et al., Chemical Abstracts, vol. 110, p. 557, abstract 23914e (1989), published in the U.S. and entitled "Preparation of N-(piperazinylbutyl)imide Derivatives as Tranquilizers and Psychotropics".

J. P. Yevich, et al., Journal of Medicinal Chemistry, vol. 26, pp. 194 to 203 (Feb. 1983), published in the U.S. and entitled "Buspirone Analogues. 1. Structure–Activity Relationships in a Series of N-Aryl- and Heteroarypiperazine Derivatives".

German Offenlegungsschrift DE 36 20 643, published Jan. 22, 1987 and English translation thereof.

Primary Examiner—Cecilia Tsang
Attorney, Agent, or Firm—Raymond R. Wittekind

[57] ABSTRACT

Novel 1-piperazinyl-2-butenes and -2-butynes, intermediates and processes for the preparation thereof, and methods of treating psychoses utilizing compounds or compositions thereof are disclosed.

6 Claims, No Drawings

1-PIPERAZINYL-2-BUTENES AND -2-BUTYNES

This is a division of application Ser. No. 07/875,477 filed Apr. 29, 1992, now U.S. Pat. No. 5,194,436 which is a division of application Ser. No. 07/639,639 filed Jan. 10, 1991. now U.S. Pat. No. 5,130,315.

The present invention relates to 1-piperazinyl-2-butenes and -2-butynes. More particularly, the present invention relates to 1-piperazinyl-2-butenes and -2-butynes of formula 1

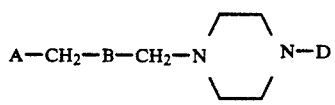

wherein A is a group of the formula

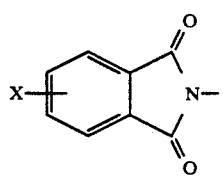

wherein X is hydrogen, halogen, alkyl, alkoxy, or trifluoromethyl; a group of the formula

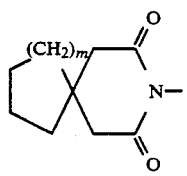

wherein m is 1 or 2; a group of the formula

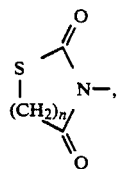

wherein n is 1 or 2; a group of the formula

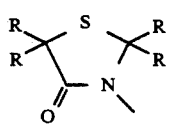

wherein R is independently hydrogen or alkyl; a group of the formula

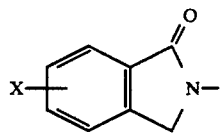

wherein X is as above; a group of the formula

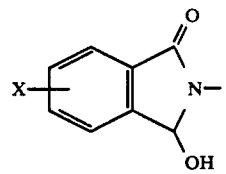

wherein X is as above; a group of the formula

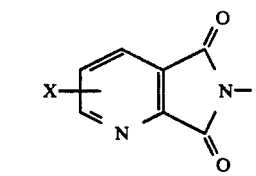

wherein X is as above; a group of the formula

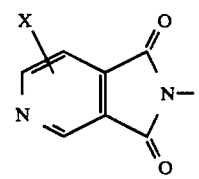

wherein X is as above; or a group of the formula

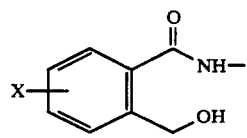

wherein X is as above; D is a group of the formula

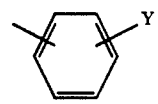

wherein Y is hydrogen, alkyl, alkoxy, halogen, or trifluoromethyl; a group of the formula

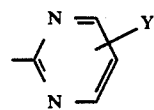

wherein Y is as above; a group of the formula

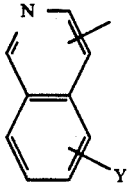

wherein Y is as above; a group of the formula

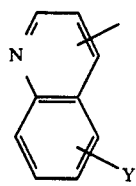

wherein Y is as above; a group of the formula

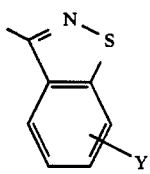

wherein Y is as above; a group of the formula

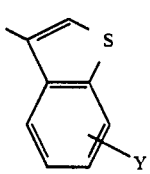

wherein Y is as above; B is C≡C,

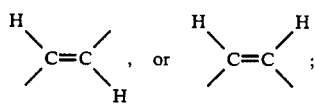

the solid line (—) refers to point of attachment of the group to the indicated member of the formula; with the provisos that (a) when A is a group of the formula

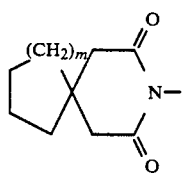

wherein m is 1 and B is C≡C, D is not a group of the formula

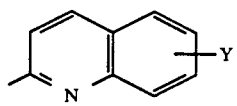

wherein Y is as above or a group of the formula

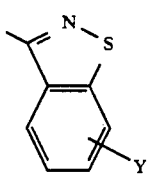

wherein Y is as above, (b) when A is a group of the formula

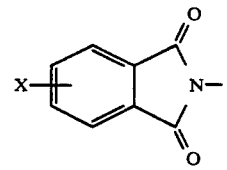

wherein X is as above and B is C≡C,

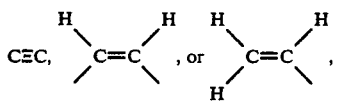

D is not a group of the formula

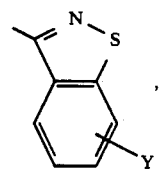

and (c) when A is a group of the formula

B is C≡C;
D is not a group of the formula

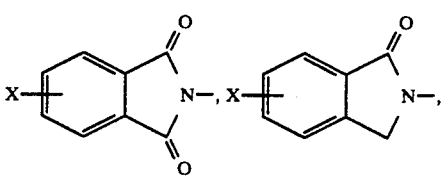

wherein Y is as above, the optical isomers thereof; or the pharmaceutically acceptable salts thereof, which are useful for treating psychoses, alone or in combination with adjuvants.

Subgeneric thereto are:

a. Compounds wherein A is a group of the formula

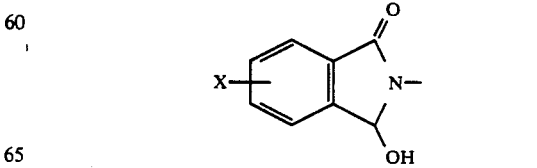

wherein X is as above;

b. Compounds wherein A is a group of the formula

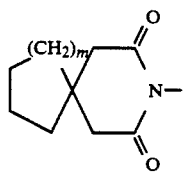

wherein m is as above;
  c. Compounds wherein A is a group of the formula

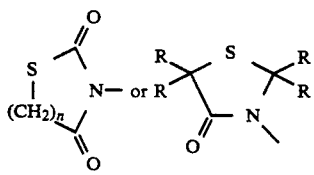

wherein R and n are as above;
  d. Compounds wherein A is a group of the formula

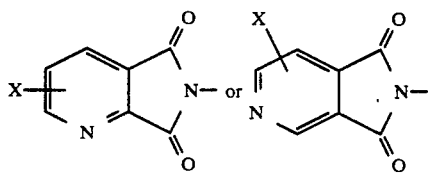

wherein X is as above;
  e. Compounds wherein A is a group of the formula

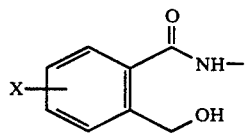

wherein X is as above; and
  f. Compounds wherein A is a group of the formula

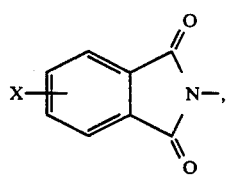

D is a group of the formula

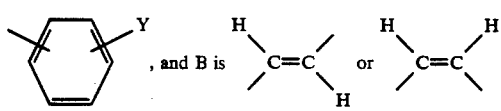

wherein X and Y are as above.

The present invention also relates to 1-amino-4-piperazinyl-2-butenes and -2-butynes of formula 2

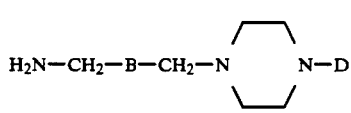

wherein B is a group of the formula

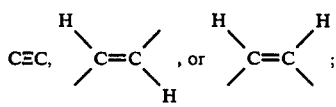

D is a group of the formula

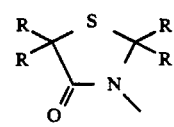

wherein Y is hydrogen, alkyl, alkoxy, halogen, or trifluoromethyl; a group of the formula

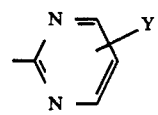

wherein Y is as above; a group of the formula

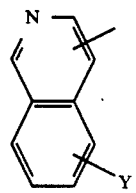

wherein Y is as above; a group of the formula

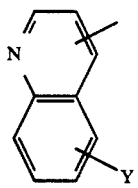

wherein Y is as above; a group of the formula

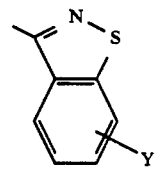

wherein Y is as above; a group of the formula

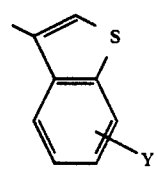

wherein Y is as above; the solid line (—) refers to point of attachment of the group to the indicated member of the formula; the optical isomers and the pharmaceutically acceptable salts thereof, and 2-(2-propargyl)-3-hydroxyisoindolones of formula 3

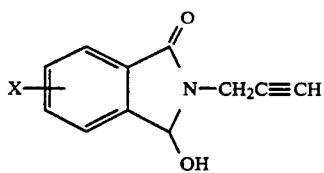

wherein X is hydrogen, halogen, alkoxy, alkyl, or trifluoromethyl; which are useful as intermediates for the preparation of the present 1-piperazinyl-2-butenes and -2-butynes.

Preferred 1-amino-4-piperazinyl-2-butenes and -2-butynes of formula 2 are those wherein D is a group of the formula

wherein Y is as hereinbeforedescribed.

As used through the specification and appended claims, the term "alkyl" refers to a straight or branched chain hydrocarbon radical containing no unsaturation and having 1 to 7 carbon atoms such as methyl, ethyl, 1-propyl, 2-propyl, 1-butyl, 1-pentyl, 2-pentyl, 3-hexyl, 4-heptyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy and the like; the term "halogen" refers to a member of a family consisting of chlorine, fluorine, bromine, or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diastereomeric salts of those instant compounds characterized by the presence of a basic amino group and optically active acid, or by the synthesis from optically active precursors.

The present invention comprehends all optical isomers and racemic forms thereof. The formulas of the compounds shown herein are intended to encompass all possible optical isomers of the compounds so depicted.

The designations "E" and "Z" refer to the arrangement of the substituents bound to the carbon-to-carbon bond of the 1-piperazinyl-2-butenes of the present invention. In the butenes designated "E", the hydrogen atoms are on opposite sides of the double bond, i.e., trans to each other. In the butenes designated "Z", the hydrogen atoms are on the same side of the double bond, i.e., cis to each other.

The novel 1-piperazinyl-2-butenes and -2-butynes of the present invention are synthesized by the processes illustrated in the reaction schemes.

To gain entry into the 1-piperazinyl-2-butyne system 8 wherein A and D are as hereinbeforedescribed, an N-propargylamide or -imide 6 wherein A is as above, commercially available or prepared by conventional methods involving the condensation of an amide or imide 4 with a propargyl halide 5 wherein Hal is chlorine or bromine in the presence of a base such as sodium carbonate or potassium carbonate, or sodium hydride in a solvent such as dimethylformamide (see M. S. Gibson and R. W. Bradshaw, Angew, Chem. Internat. Edit.; 7, 919 (1968), is animated with a piperazine 7 wherein D is as above in the presence of formaldehyde or an equivalent thereof such as paraformaldehyde. The amination is conducted in the presence of a promoter and an acid acceptor in a ethereal solvent. Among promoters there may be mentioned copper (I) and copper (II) chloride. Among acid acceptors there may be mentioned tertiary amines such as, for example, trialkylamines, i.e., trimethylamine, triethylamine, tripropylamine and the like, and heteroaromatic amines such as, for example, pyridine and alkyl derivatives thereof, i.e., picoline, lutidine, and collidine. Among ethereal solvents there may be mentioned diethyl ethyl, 1,2-dimethoxyethane, 2-methoxyethyl ether, dioxane, and tetrahydrofuran. Preferred acid acceptors are trialkylamines. Most preferred is triethylamine. Preferred solvents are dioxane and tetrahydrofuran. While the amination temperature is not narrowly critical, it is preferred to conduct the amination at a temperature between about ambient temperature and the reflux temperature of the reaction medium, the reflux temperature of the reaction medium being preferred.

To fabricate a 1-piperazinyl-2-butene 9, a 1-piperazinyl-2-butyne 8 is reduced catalytically to provide the Z-isomer 9. The catalytic reduction is performed by means of hydrogen at about atmospheric pressure and about room temperature in the presence of a metal catalyst such as platinum, palladium, rhodium, or ruthenium, unsupported or supported on carbon, calcium carbonate, or barium sulfate, e.g., platinium-on-carbon, palladium-on-carbon, or palladium-on-barium sulfate. Palladium-on-barium sulfate is preferred. A solvent is normally employed. Included among solvents are alcohols (e.g., methanol, ethanol, 2-propanol, and the like), halocarbons (e.g., dichloromethane, trichloromethane, 1,1- and 1,2-dichloroethane, and the like), ethers (e.g., 1,2-dimethoxyethane, 2-methoxyethyl ether, tetrahydrofuran, dioxane, and the like), and esters (e.g., methyl acetate, ethyl acetate, methyl propionate, and the like) and combinations thereof (e.g., methanol/tetrahydrofuran, ethyl acetate/dichloromethane, ethanol/tetrahydrofuran, ethanol/ethyl acetate, and the like). See Reaction Scheme A.

To prepare an E-1-piperazinyl-2-butene 10, a piperazinyl-2-butyne 8 wherein A is, for example, a group of the formula

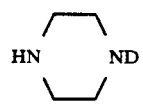

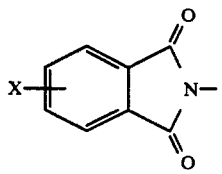

is aminolyzed with a primary amine, e.g., an alkylamine such as methylamine, in an aqueous halocarbon, e.g., dichloromethane, at about ambient temperature to provide a 1-amino-2-butyne 12 which is reduced catalytically to a Z-1-amino-2-butene 13 by the process for the conversion of 8 to 9, or chemically to an E-1-amino-2-butene 14.

The chemical reduction is performed by means of an alkali metal aluminohydride in an ethereal solvent at a temperature within the range of about 0° to about the reflux temperature of the reduction medium. Alkali metal aluminohydrides include lithium aluminum hydride, sodium aluminum hydride, and potassium aluminum hydride. Ethereal solvents include diethyl ether, 1,2-dimethoxyethane, 2-methoxyethyl ether, dioxane, and tetrahydrofuran. A reduction medium consisting of lithium aluminum hydride and tetrahydrofuran and a reduction temperature of about 5° to about 25° C. is preferred. See Reaction Scheme B.

Alternatively, a 1-piperazinyl-2-butyne 8 and Z- and E-1-piperazinyl-2-butenes 9 and 10 are prepared by condensing an anhydride, for example, a phthalic anhydride 15 wherein X is as hereinbeforedescribed, with a 1-amino-2-butyne 12, a Z-1-amino-2-butene 13, or an E-1-amino-2-butene 14, respectively. The condensation is accomplished by treating an anhydride 15 with an amine 12, 13, or 14 in the presence of a tertiary amine, e.g., a trialkylamine such as trimethylamine, triethylamine, or tripropylamine, or a heteroaromatic amine such as pyridine, picoline, lutidine, or collidine, in a aromatic solvent, e.g., benzene and alkylated benzenes such as toluene, xylene, and mesitylene at the reflux temperature of the reaction medium with water removal. Alkylated benzenes are the preferred solvents. Xylene (or xylenes) is most preferred. While the condensation proceeds readily under the aforedescribed conditions, a promoter such as acetic anhydride may be employed. See Reaction Scheme B.

The reaction sequence illustrated in Reaction Scheme B can be carried out with piperazinyl-2-butynes 8 wherein A is, for example,

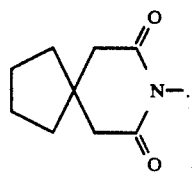

E-1-Piperazinyl-2-butenes 10 wherein A and D are as hereinbeforedescribed are also elaborated by condensation of an amide or imide 4 wherein A is as above with an E-1,4-dihalo-2-butene 20

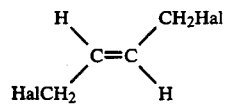

wherein Hal is chloro or bromo in the presence of an alkali metal hydride (e.g., sodium hydride) in a polar aprotic solvent (e.g., dimethylformamide) to provide an E-1-halo-2-butene 19 wherein Hal is as hereinbeforedescribed (see R. B. Wagner and H. D. Zook, Synthetic Organic Chemistry, John Wiley and Son, Inc. New York, N.Y., 1953, page 572), which is coupled with a piperazine to afford 10. The coupling is carried out in an alkylnitrile (e.g., acetonitrile) in the presence of a base (e.g., an alkali metal carbonate or bicarbonate such as sodium or potassium carbonate or bicarbonate) and a promoter (e.g., an alkali metal halide such as sodium or potassium iodide) at a temperature within the range of about 40° C. to the reflux temperature of the coupling reaction medium. Preferred reaction conditions are acetonitrile as the solvent, potassium carbonate as the base, sodium iodide as the promoter, and about 75° C. as the reaction temperature. See Reaction Scheme C.

An E-1-piperazinyl-2-butene 10 is also synthesized by construction of the A-moiety from an E-1-amino-2-butene 14. Thus, for example, to prepare an E-1-(3-thiazolidine-2,4-dione)-4-piperazine-2-butene 10 wherein A is a

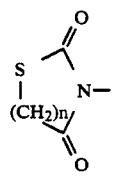

wherein n is 1, a butene 14 is treated with an alkyl thioglycolate 23

ROCOCH$_2$SH    23 wherein R is alkyl in an aromatic hydrocarbon solvent such as, for example, toluene, followed by carbonyldiimidazole, at the reflux temperature of the reaction medium. The corresponding Z-2-butene 9 and 2-butyne 8 may be prepared from the appropriate precursors 13 and 12, respectively.

As hereinbeforedisclosed, 1-amido-4-piperazinyl-2-butyne 8, a Z- and an E-2-butene 9 and 10 wherein A is a group of the formula

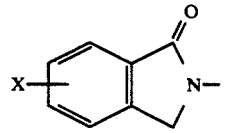

are synthesized by the processes delineated in Reaction Scheme D. For example, reduction of a phthalimido-2-butyne (24 wherein B is C≡C) or a -2-butene (24 wherein B is

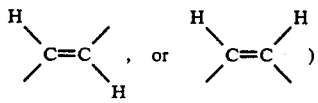

with an alkali metal borohydride, e.g., lithium borohydride, sodium borohydride, or potassium borohydride, in an alkanol, e.g., methanol, ethanol, or 2-propanol, and a halocarbon, e.g., dichloromethane, trichloromethane, or 1,2-dichloromethane, affords hydroxyisoindolonobutyne (25 wherein B is C≡C) or -butene (25 wherein B is

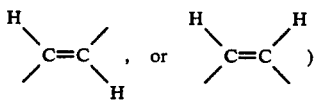

and a hydroxymethylbenzamidobutyne (26 wherein B is C≡C) and -butene (26 wherein B is

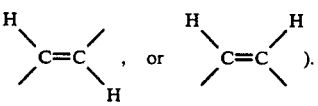

Sodium borohydride in methanol/dichloromethane is the preferred reduction system. The reduction temperature is not narrowly critical. A reduction temperature of about 0° to about 50° C. is preferred. A reduction temperature of about 25° C. is most preferred.

Removal of the hydroxyl group of a hydroxyisoindolonobutyne (25 wherein B is C≡C) or -butene (25 wherein B is

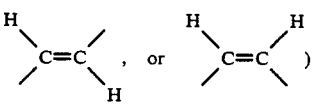

to yield a isoindolonobutyne (27 wherein B is C≡C) or -butene (27 wherein B is

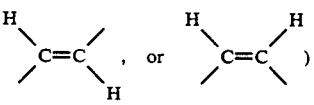

is conveniently accomplished by contacting 25 with a trialkylsilane 28

wherein $R_1$ is alkyl such as triethylsilane, in the presence of a strong organic acid such as trifluoroacetic acid in a halocarbon solvent such as dichloromethane at about ambient temperature.

A Z-1-amido-4-piperazinyl-2-butene 27 (wherein B is

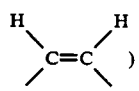

may be prepared by catalytic reduction of a 1-amido-4-piperazinyl-2-butyne 27 (wherein B is C≡C) by the process described for the conversion of 8 to 9 on page 9, lines 9 to 21, of the specification and illustrated in Reaction Scheme A.

Compounds of the invention include:
a. 1-(N-4-methylphthalimido)-4-[4-(3-trifluoromethylphenyl)-1-piperazinyl]-2-butyne;
b. Z-1-(N-5-methoxyphthalimido)-4-[4-(3-trifluoromethylphenyl)-1-piperazinyl]-2-butene;
c. E-1-(3-trifluoromethylphenylphthalimido)-4-[4-(3-trifluoromethylphenyl)-1-piperazinyl]-2-butene;
d. 1-(N-phthalimido)-4-[4-(3-methylphenyl)-1-piperazinyl]-2-butyne;
e. 1-(N-phthalimido)-4-[4-(benzo[b]thiophen-3-yl)-1-piperazinyl]-2-butyne
f. Z-1-amino-4-[4-benzo[b]thiophen-3-yl)-1-piperazinyl]-2-butene.
g. Z-1-(N-phthalimido)-4-[4-(4-methoxyphenyl)-1-piperazinyl]-2-butene; and
h. E-1-(N-phthalimido)-4-[4-(5-chlorophenyl)-1-piperazinyl]-2-butene.
i. 1-[3-(2-methyl-4-thiazolidinone)]-4-(4-[1,2-benzisothiazol-3-yl)-1-piperazinyl]-2-butene.
j. 1-[3-(5-methyl-4-thiazolidinone)]-4-(4-[1,2-benzisothiazol-3-yl)-1-piperazinyl]-2-butene.

The 1-piperazinyl-2-butenes and -2-butynes of the present invention are useful for treating psychoses by virtue of their ability to block apomorphine-induced climbing in mammals.

Antipsychotic activity is determined in the climbing mice assay by methods similar to those described by P. Protais et al., Psychopharmacol., 50, 1 (1976) and B. Costall, Eur. J. Pharmacol., 50, 39 (1978).

The subject CK-1 male mice (23–27 grams) are ground-housed under standard laboratory conditions. The mice are individually placed in wire mesh stick cages (4"×4"10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20, and 30 minutes after apomorphine administration according to the following scale:

| Climbing Behavior | Score |
|---|---|
| Mice with: | |
| 4 paws on bottom (no climbing) | 0 |
| 2 paws on wall (rearing) | 1 |
| 4 paws on the wall (full climbing) | 2 |

Mice consistently climbing before the injections of apomorphine will be discarded.

With full-developed apomorphine climbing, the animals are hanging onto the cage walls, rather motionless, over long periods of time. By contrast, climbs due to mere motor stimulation usually only last a few seconds.

The climbing scores are individually totaled (maximal score: 6 per mouse over 3 readings) and the total score of the control group (vehicle intraperitoneally-apomorphine subcutaneously) is set 100%. $ED_{50}$ values with 95% confidence limits are calculated by a Linear Regression Analysis. Antipsychotic activity expressed as the $ED_{50}$ value of representative 1-piperazinyl-2- butenes and -2-butynes as well as two standard antipsychotics are presented in Table II.

TABLE II

| Compound | Antipsychotic Activity ED$_{50}$ (mg/kg) |
|---|---|
| Z-1-(3-thiazolidine-2,4-dione)-4-[4-(2-methoxyphenyl)-1-piperazinyl]-2-butene | 19.8 |
| Z-1-(N-phthalimido)-4-[4-(2-methoxyphenyl)-1-piperazinly]-2-butene | 10.3 |
| E-1-(N-phthalimido)-4-[4-(2-methoxyphenyl)-1-piperazinyl]-2-butnen | 7.3 |
| Z-1-[N-(4-chlorophthalimido)-4-(4-(2-methoxyphenyl)-1-piperazinyl]-2-butene | 15.4 |
| Haloperidol (Standard) | 0.11 |
| Sulpiride (Standard) | 4.5 |

Antipsychotic activity is achieved when the present 1-piperazinyl-2-butenes and -2-butynes are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted to the individual need and the professional judgment of the person administering of supervising the administration of aforesaid compound. It is to be further understood that the dosages set forth herein are exemplary only and they do not, to any extent, limit the scope or practice of the invention.

Effective amounts of the compounds of the invention may be administered to a subject by any one of various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically, acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition in such that a suitable dosage will be obtained. Preferred compositions and preparations according to the present invention are prepared so that an oral dosage unit form contains between 1.0–3.00 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

1-(N-Phthalimido)-4-[4-(3-trifluoromethylphenyl)-1-piperazinyl]-2-butyne

A suspension of N-propargylphthalimide (85.0 g), m-trifluoromethylphenyl-1-piperazine hydrochloride (123 g), paraformaldehyde (19.3 g), copper (I) chloride (9.18 g), and triethylamine (46.5 g) in anhydrous tetrahydrofuran (1200 ml) was heated under reflux for 6 hrs. The reaction mixture was concentrated and the residue was chromatographed (200 g silica gel, eluted with ethyl acetate). The appropriate fractions were collected and concentrated. The residue was recrystallized from ethyl acetate:hexane to give product, mp 118°–120° C.

| ANALYSIS: | | | |
|---|---|---|---|
| Calculated for $C_{23}H_{20}F_3N_3O_2$: | 64.53% C | 4.72% H | 9.83% N |

-continued

| ANALYSIS: | | | |
|---|---|---|---|
| Found: | 64.45% C | 4.72% H | 9,91% N |

EXAMPLE 2

Z-1-(N-Phthalimido)-4-[4-(3-trifluoromethylphenyl)-1-piperazinyl]-2-butene

A solution containing 2.50 g of 1-(N-phthalimido)-4-[4-(3-trifluoromethylphenyl)-1-piperazinyl]-2-butyne, methanol (200 ml), and tetrahydrofuran (20 ml) was evacuated and then purged with hydrogen gas three times. 5% Palladium-on-barium sulfate (0.12 g) was added. After 150 ml of hydrogen was consumed, the reaction mixture was filtered through a bed of celite. The filter cake was washed with methanol and the filtrate was evaporated. The residue was purified by column chromatography (silica gel, eluted with 25% ethyl acetate:dichloromethane). The appropriate fractions were collected and evaporated. Recrystallization of the residue from hexane gave 2.10 g (84% of theory) of product, mp 76°–79° C.

| ANALYSIS: | | | |
|---|---|---|---|
| Calculated for $C_{23}H_{22}F_3N_3O_2$: | 64.32% C | 5.16% H | 9.78% N |
| Found | 64.44% C | 4.89% H | 9.92% N |

EXAMPLE 3

E-1-(N-Phthalimido)-4-[4-(3-trifluoromethylphenyl)-1-piperazinyl]-2-butene

A solution of E-1-amino-4-[(4-(3-trifluoromethylphenyl)-1-piperazinyl)]-2-butene (3.00 g), phthalic anhydride (1.75 g), xylene (50ml), and pyridine (2 ml) was refluxed for 19 hours. The reaction mixture was concentrated and the residue was chromatographed (60 g silica gel, eluted with 35% ethyl acetate:dichloromethane). The appropriate fractions were collected and concentrated to afford 3.67 g (85%) of product. Recrystallization from hexane gave the analytical sample, mp 83°–85° C.

| ANALYSIS: | | | |
|---|---|---|---|
| Calculated for $C_{23}H_{22}F_3N_3O_2$: | 64.32% C | 5.16% H | 9.78% N |
| Found | 64.30% C | 5.26% H | 9.76% N |

EXAMPLE 4

1-(N-Phthalimido)-4-[4-(2-methoxyphenyl)-1-piperazinyl]-2-butyne dihydrochloride A suspension of N-propargylphthalimide (48.5 g), 1-(2-methoxyphenyl)piperazine hydrochloride (61.1 g), paraformaldehyde (11.1 g), triethylamine (29.1 g), and copper (I) chloride (10.4 g), in anhydrous tetrahydrofuran (1200 ml) was heated under reflux for 2.5 hrs. The reaction mixture was washed with 0.43M aqueous sodium hydroxide solution (600 ml), two portions of water (1 l), brine (1 l), dried over anhydrous sodium sulfate, filtered, and the filtrate was concentrated. The residue was triturated with diethyl ether to give 82.5 g (81%) of product as a free base. The dihydrochloride was prepared by dissolving 19 g of the free base in dichloromethane (300 ml) and treating the solution with excess ethereal hydrogen chloride. The salt was collected, washed with diethyl ether, and dried at 50° C. (150 mm) for 16 hrs to afford 22.5 g of product, mp 191°–194° C.

| ANALYSIS: | | | |
|---|---|---|---|
| Calculated for $C_{23}H_{23}N_3O_3.2HCl$ | 59.74% C | 5.45% H | 9.09% N |
| Found: | 59.23% C | 5.59% H | 9.12% N |

EXAMPLE 5

E-1-(N-Phthalimido)-4-[4-(2-methoxyphenyl)-1-piperazinyl]-2-butene hydrochloride hemihydrate A solution of phthalic anhydride (2.81 g), E-1-amino-4-[4-(2-methoxyphenyl)-1-piperazinyl]-2-butene (4.80 g) and toluene (125 ml) was heated under reflux, with water collection in a Dean-Stark trap. After 1.5 hrs., acetic anhydride (1.94 g) and pyridine (2 ml) were added, and the reaction mixture was refluxed for an additional 2 hrs. The reaction mixture was diluted with ethyl acetate (200 ml) and washed with 5% aqueous copper sulfate (300 ml), water (300 ml), brine (300 ml), dried over anhydrous sodium sulfate, filtered, and the filtrate was concentrated. The residue was purified by column chromatography (100 g silica gel, eluted with 35% ethyl acetate:dichloromethane). The appropriate fractions were collected and concentrated. The residue was dissolved in dichloromethane (10 ml) and the solution was treated with excess ethereal hydrogen chloride. The mixture was evaporated and the residue was recrystallized from water to afford 1.80 g (22%) of product, mp 198°–201° C.

| ANALYSIS: | | | |
|---|---|---|---|
| Calculated for $C_{23}H_{25}N_3O_3.HCl.1.5H_2O$: | 63.22% C | 6.23% H | 9.62% N |
| Found: | 63.46% C | 6.16% H | 9.66% N |

EXAMPLE 6

Z-1-(N-Phthalimido)-4-[4-(2-methoxyphenyl)-4-piperazinyl)]-2-butene dihydrochloride A solution of 1-(N-phthalimidoyl)-4-[4-(2-methoxyphenyl)-1-piperazinyl]-2-butyne dihydrochloride (8.00 g) and methanol (400 ml) was evacuated and then purged with hydrogen gas three times in an atmospheric pressure hydrogenation apparatus. 5% Palladium-on-barium sulfate (0.40 g) was added. After 500 ml of hydrogen gas was consumed, the reaction mixture was filtered through a bed of celite, the filter cake washed with methanol (50 ml), and the filtrate was concentrated. Recrystallization of the residue from dichloromethane:ether gave 6.81 g (84%) of product, mp 199°–203° C.

| ANALYSIS: | | | |
|---|---|---|---|
| Calculated for $C_{23}H_{25}N_3O_3 2HCl$: | 59.48% C | 5.86% H | 9.05% N |
| Found: | 58.98% C | 5.91% H | 8,92% N |

EXAMPLE 7

1-N-(4-Chlorophthalimido)-4-[4-(2-methoxyphenyl)-1-piperazinyl]-2-butyne

A solution of 4-chlorophthalic anhydride (4.57 g), E-1-amino-4-[4-(2-methoxyphenyl)-1-piperazinyl]-2-butyne (5.90 g), toluene (150 ml), and pyridine (4 ml) was heated under reflux with water collection in a Dean-Stark apparatus. After 18.5 hrs., acetic anhydride (4 ml) was added, and the reaction mixture was refluxed for an additional 3.5 hrs. The reaction mixture was evaporated and the residue was dissolved in dichloromethane (300 ml), washed with 5% aqueous sodium bicarbonate solution (100 ml), water (200 ml), brine (200 ml), dried over anhydrous sodium sulfate, filtered, and the filtrate was concentrated. The residue was purified by column chromatography (300 g silica gel, eluted with 40%-ethyl acetate:hexane). The appropriate fractions were collected and concentrated. Recrystallization of the residue from ethyl acetate:pentane gave 2.63 g (27%) of product, mp 94°–97° C.

| ANALYSIS: | | | |
|---|---|---|---|
| Calculated for $C_{23}H_{22}ClN_3O_3$: | 65.17% C | 5.23% H | 9.91% N |
| Found: | | 64.83% C | 5.26% H | 10.06% N |

EXAMPLE 8

Z-1-N-(4-Chlorophthalimido)-4-[4-(2-methoxyphenyl)-1-piperazinyl]-2-butene dihydrochloride hemihydrate A solution of 1-N-(4-chlorophthalimido)-4-[4-(2-methoxyphenyl)-1-piperazinyl]-2-butyne dihydrochloride (2.51 g) and methanol (300 ml) was evacuated and purged with hydrogen gas three times in an atmospheric pressure hydrogenation apparatus. 5% Palladium-on-barium sulfate (0.12 g) was added. After 125 ml of hydrogen gas was consumed, the reaction mixture was filtered through a bed of celite, the filter cake was washed with methanol (50 ml), and the filtrate was evaporated. 10% Aqueous sodium hydroxide solution was added to the residue and the mixture was extracted with dichloromethane (200 ml). The extract was purified by column chromatography (silica gel, eluted with 35% ethyl acetate:dichloromethane). The appropriate fractions were collected and concentrated. The residue was dissolved in dichloromethane and treated with a slight excess of ethereal hydrogen chloride. Pentane was added. The precipitate was collected, washed with pentane, and dried to provide 1.75 g (70%) of product, mp 215°–218° C.

| ANALYSIS: | | | |
|---|---|---|---|
| Calculated for $C_{23}H_{24}ClN_3O_3 \cdot 2HCl \cdot 0.5H_2O$: | 54.39% C | 5.36% H | 8.27% N |
| Found: | 54.63% C | 5.51% H | 8.08% N |

EXAMPLE 9

E-1-N-(4-Chlorophthalimido)-4-[4-(3-trifluoromethylphenyl)-1-piperazinyl]-2-butene dihydrochloride To a 0° C. solution of E-1-amino-4-[4-(3-trifluoromethylphenyl)-1-piperazinyl)]-2-butene (3.50 g) in xylene (50ml), was added 4-chlorophthalic anhydride (3.65 g). The solution was stirred at room temperature for 15 hrs and pyridine (4 ml) was added. The reaction mixture was heated under reflux for 7 hrs, and the solvent was evaporated. The residue was purified by column chromatography. The appropriate fractions were collected and evaporated. The residue was dissolved in 1:1-ether:dichloromethane and the solution was treated with ethereal hydrogen chloride. The precipitate was collected, washed with pentane, and dried to provide 1.78 g (28%) of product, mp 170°–177° C.

| ANALYSIS: | | | |
|---|---|---|---|
| Calculated for $C_{23}H_{21}ClF_3N_3O_2 \cdot 2HCl$: | 51.46% C | 4.32% H | 7.83% N |
| Found: | 51.31% C | 4.30% H | 7.85% N |

EXAMPLE 10

1-N-(Phthalimido)-4-[4-(2-pyrimidino)-1-piperazinyl]-2-butyne

A suspension of N-propargylphthalimide (15.36 g), 1-(2-pyrimidyl)piperazine dihydrochloride (19.7 g), paraformaldehyde (3.49 g) and copper (II) chloride (3.29 g), in triethylamine (12 ml) and tetrahydrofuran (160 ml) was heated under reflux for 19 hrs and allowed to cool to room temperature. 25% Aqueous sodium hydroxide solution (11 ml) and dichloromethane (200 ml) were added. The precipitate was collected and the filtrate was washed with water, brine, dried over anhydrous magnesium sulfate, filtered, and the filtrate was concentrated. Recrystallization of the residue from ethyl acetate:hexane provided 24.8 g (83%) of product, mp 153°–155° C.

| ANALYSIS: | | | |
|---|---|---|---|
| Calculated for $C_{20}H_{19}N_5O_2$: | 66.46% C | 5.30% H | 19.38% N |
| Found: | 66.21% C | 5.40% H | 19.11% N |

EXAMPLE 11

Z-1-(N-Phthalimido)-4-[4-(2-pyrimidino)-1-piperazinyl]-2-butene

A solution of 1-(N-phthalimido)-4-[4-(2-pyridimino)-1-piperazinyl]-2-butyne (10.4 g), absolute ethanol (200 ml), ethyl acetate (100 ml), dichloromethane (100 ml), and quinoline (1 ml) was degassed by evacuation followed by purging with hydrogen gas three times in an atmospheric pressure hydrogenation apparatus. 5% Palladium-on-barium sulfate (0.51 g) was added. A total of 700 ml hydrogen gas was absorbed. The mixture was filtered and the filtrate was evaporated. The residue was purified by column chromatography (150 g silica gel, eluted with ethyl acetate). The appropriate fractions were collected and concentrated. Recrystallization of the residue from ethyl acetate:hexane gave 8.31 g (80%) of product, mp 138°–140° C.

| ANALYSIS: | | | |
|---|---|---|---|
| Calculated for $C_{20}H_{21}N_5O_2$: | 66.10% C | 5.82% H | 19.27% N |
| Found: | 66.10% C | 5.85% H | 19.37% N |

EXAMPLE 12

1-N-(Phthalimido)-4-[4-(3-isoquinolino)-1-piperazinyl]-2-butyne

A suspension of N-propargylphthalimide (2.61 g), 3-(1-piperazinyl)isoquinoline (3.00 g), paraformaldehyde (0.60 g), copper (II) chloride (0.55 g) and tetrahydrofuran (75 ml) was heated to reflux. After 22 hrs, the reaction mixture was allowed to cool and was passed through a silica gel column (50 g), eluting with ethyl acetate. The eluate was chromatographed (60 g silica gel, eluted with 35% ethyl acetate:dichloromethane). The appropriate fractions were collected and evaporated to give 2.43 g (42%) of product. Recrystallization from ethyl acetate:hexane provided the analytical sample, mp 169°–171° C.

| ANALYSIS: | | | |
|---|---|---|---|
| Calculated for $C_{25}H_{22}N_4O_2$: | 73.51% C | 5.40% H | 13.65% N |
| Found: | 72.62% C | 5.36% H | 13.48% N |

EXAMPLE 13

1-(N-Phthalimido)-4-[4-(2-quinolino)-1-piperazinyl]-2-butyne

A suspension of N-propargylphthalimide (37.0 g), 2-(1-piperazinyl)quinoline (42.7), paraformaldehyde (8.40 g), and copper (I) chloride (7.92 g), in tetrahydrofuran (700 ml) was heated under reflux. After 4 hrs, the reaction mixture was allowed to cool to room temperature and 2.5% aqueous sodium hydroxide solution (10 ml) and water (10 ml) were added. The mixture was filtered and the filtrate was divided into two equal portions. Each was concentrated. The residues were purified by column chromatography (450 g silica gel, eluted with 1:1-dichlormethane:ethyl acetate). The appropriate fractions were collected and evaporated. Recrystallization of the residue from ethyl acetate:hexane provided a total of 60.4 g (74%) of product, mp 152°–154° C.

| ANALYSIS: | | | |
|---|---|---|---|
| Calculated for $C_{25}H_{22}N_4O_2$: | 73.15% C | 5.40% H | 13.65% N |
| Found: | 73.10% C | 5.48% H | 13.59% N |

EXAMPLE 14

Z-1-(N-Phthalimido)-4-[4-(2-quinolino)-1-piperazinyl]-2-butene

A solution of 1-(Nphthalimido)-4-[4-(2-quinolino)-1-piperazinyl]-2-butyne (3.00 g), in tetrahydrofuran (150 ml) and absolute ethanol (150 ml) was evacuated and purged three times with hydrogen gas in an atmospheric pressure hydrogenation apparatus. 5% Palladium-on-barium sulfate (0.15 g) was added. After a total of 180 ml of hydrogen gas was absorbed, the suspension was filtered through a bed of celite and the filtrate was concentrated. The residue was passed through a 50 g-silica gel column, eluting with ethyl acetate. The eluent was evaporated and the residue was crystallized with ethyl acetate:hexane to provide 2.35 g (78%) of product, mp 134°–136° C.

| ANALYSIS: | | | |
|---|---|---|---|
| Calculated for $C_{25}H_{24}N_4O_2$: | 72.79% C | 5.86% H | 13.58% N |
| Found: | 72.72% C | 5.74% H | 13.56% N |

EXAMPLE 15

E-1-[8-(8-Azaspiro[4.5]decane-7,9-dione)[-4-(3-trifluoromethylphenyl)-1-piperazinyl]-2-butene dihydrochloride A solution of 3,3-tetramethyleneglutaric anhydride (1.90 g), E-1-amino-4-[4-(3-trifluoromethylphenyl)-1-piperazinyl]-2-butene, xylenes (50 ml) and pyridine (2 ml) was heated under reflux. After 19 hr, the reaction mixture was evaporated and the residue was purified by flash chromatography (50 g silica gel, eluted with 35% ethyl acetate:dichloromethane). The appropriate fractions were collected and evaporated. The residue was treated with ethereal hydrogen chloride to give 3.66 g (70%) of product, mp 158°–164° C.

| ANALYSIS: | | | |
|---|---|---|---|
| Calculated for $C_{24}H_{30}F_3N_3O_2 \cdot 2HCl$: | 55.17% C | 6.17% H | 8.04% N |
| Found: | 55.27% C | 6.25% H | 7.92% N |

EXAMPLE 16

E-1-(3-Thiazolidine-2,4-dione)-4-[4-(2-methoxyphenyl)-1-piperazinyl]-2-butene dihydrochloride A solution of methyl thioglycolate (1.95 g), E-1-amino-4-[4-(2-methoxyphenyl-1-piperazinyl)-2-butene (4.00 g) and toluene (250 ml) was heated under reflux with water separation with a Dean-Stark apparatus for 20 hrs. After cooling to room temperature, carbonyldiimidazole (3.24 g) was added and the reaction mixture was refluxed for 24 hrs. The reaction mixture was evaporated and the residue was purified by column chromatography (150 g silica gel, eluted with 35% ethyl acetate:dichloromethane (1 l), 50% ethyl acetate:dichloromethane (1 l), and ethyl acetate (1 l). The appropriate fractions were collected and evaporated to provide 4.00 g (72%) of product, as the free base. The base was dissolved in dichloromethane and treated with excess ethereal hydrogen chloride. The precipitate was filtered, washed with dichloromethane, ether and dried to provide product, mp 208°–211° C.

| ANALYSIS: | | | |
|---|---|---|---|
| Calculated for $C_{18}H_{23}N_3O_3S \cdot 2HCl$: | 49.77% C | 5.80% H | 9.67% N |
| Found: | 49.43% C | 5.79% H | 9.63% N |

EXAMPLE 17

1-(3-Thiazolidine-2,4-dione)-4-[4-(2-methoxyphenyl)-1-piperazinyl]-2-butyne dihydrochloride A suspension of N-propargyl-2,4-thiazolidinedione (35.9 g), 1-(2-methoxyphenyl)piperazine hydrochloride (54.1 g), paraformaldehyde (9.74 g), triethylamine (25.5), copper (I) chloride (7.50 g) and dioxane (1000 ml) was heated to 85° C. After 1.25 hrs, ice was added to cool the reaction mixture to room temperature and the pH was adjusted to 8 with saturated sodium bicarbonate solution. The reaction mixture was diluted with water (1.5 l) and the aqueous phase was extracted with three one liter-portions of dichloromethane. The combined organic layers were filtered and divided into two equal portions; each was washed twice with water (1 l), brine (1 l), dried over anhydrous sodium sulfate, filtered, and the filtrate was concentrated. The residue was purified by high performance liquid chromatography (2 silica gel columns, eluted with 15% ethyl acetate:dichloromethane). The appropriate fractions were collected and concentrated. A 10.4 g-sample of the residue was dissolved in dichloromethane (500 ml) and treated with excess ethereal hydrogen chloride. The precipitate was collected and dried to give 9.90 g (79%) of product, mp 192°–198° C.

| ANALYSIS: | | | |
|---|---|---|---|
| Calculated for $C_{18}H_{21}N_3O_3S \cdot 2HCl$: | 50.00% C | 5.36% H | 9.72% N |
| Found: | 49.65% C | 5.68% H | 9.88% N |

EXAMPLE 18

Z-1-(3-Thiazolidine-2,4-dione)-4-[4-(2-methoxyphenyl)-1-piperazinyl]-2-butene dihydrochloride A solution of 1-(3-thiazolidine-2,4-dione)-4[4-(2-methoxyphenyl)-1-piperazinyl]-2-butyne dihydrochloride and methanol (400 ml) was evacuated and purged with hydrogen gas three times in an atmospheric pressure hydrogenation apparatus. 5% Palladium-on-barium sulfate (0.50 g) was added. After 1.5 hrs, 325 ml of hydrogen was absorbed. The reaction mixture was filtered through a bed of celite and the filtrate was concentrated. Recrystallization of the residue from dichloromethane:ether gave 4.20 g (84%) of product, mp 197°–202° C. (dec).

| ANALYSIS: | | | |
|---|---|---|---|
| Calculated for $C_{18}H_{23}N_3O_3S \cdot 2HCl$: | 49.77% C | 5.80% H | 9.67% N |
| Found: | 49.54% C | 5.81% H | 9.63% N |

EXAMPLE 19

E-1-[3-(4-Thiazolidinone)]-4-[4-(1,2-benzisothiazol-3-yl)-1-piperazinyl]-2-butene A mixture of E-1-[3-(4-thiazolidinone)]-4-bromo-2-butene (5.00 g), 1-(1,2-benzisothiazol-3-yl)piperazine hydrochloride (5.69 g), potassium carbonate (11.7 g), sodium iodide (290 mg) and acetonitrile (220 ml) was heated at 75° C. under nitrogen for 24 hrs. The reaction mixture was cooled to ambient temperature and filtered. The filter cake was washed with dichloromethane and the filtrate was concentrated. The residue was dissolved in dichloromethane (220 ml), washed with water (150 ml), brine (150 ml), dried over anhydrous sodium sulfate, filtered, and the filtrate was concentrated. The residue was chromatographed on silica gel, eluting with 5% methanol in dichloromethane. The appropriate fractions were collected and concentrated. Recrystallization of the residue from ether:hexanes gave 1.90 (23.9%) of product, mp 68°–70° C.

| ANALYSIS: | | | |
|---|---|---|---|
| Calculated for $C_{18}H_{22}N_4OS_2$: | 57.75% C | 5.92% H | 14.96% N |
| Found: | 57.76% C | 5.80% H | 14.83% N |

EXAMPLE 20

1-(2-Isoindol-1-ono)-4-[4-(2-quinolino)-1-piperazinyl]-2-butyne

Triethylsilane (2.46 ml, 1.79 g) was added to a solution of 1-(3-hydroxy-2-isoindol-1-ono)-4-[4-(2-quinolino)-1-piperazinyl]-2-butyne (4.63 g), trifluoroacetic acid (17 ml) and dichloromethane (20 ml) at room temperature. The reaction mixture was evaporated and the solution was treated with saturated sodium bicarbonate solution until the aqueous phase was basic. The aqueous layer was extracted with dichloromethane (200 ml), and the organic phase was washed with brine (200 ml), dried over anhydrous sodium sulfate, filtered, and the filtrate was concentrated. The residue was purified by column chromatography (50 g silica gel, sequentially eluted with hexane and ethyl acetate). The appropriate fractions were collected and concentrated to provide 4.13 g (93%) of product. Recrystallization from ethyl acetate gave the analytical sample, mp 121°–123° C.

| ANALYSIS: | | | |
|---|---|---|---|
| Calculated for $C_{25}H_{24}N_4O$: | 75.73% C | 6.10% H | 14.13% N |
| Found: | 75.53% C | 6.14% H | 14.09% N |

EXAMPLE 21

Z-1-(2-Isoindol-1-ono)-4-[4-(2-quinolino)-1-piperazinyl]-2-butene

A solution of 1-(2-isoindol-1-ono)-4-[4-(2-quinolino)-1-piperazinyl]-2-butyne (2.63 g), absolute ethanol (150 ml) and ethyl acetate (25 ml) was degassed and purged with hydrogen gas three times in an atmospheric pressure hydrogenation apparatus. 5% Palladium-on-barium sulfate (0.13 g) was added. Hydrogen (162 ml) was absorbed. The reaction mixture was filtered through a bed of celite and washed with ethyl acetate. The filtrate was concentrated. The residue was purified by column chromatography (60 g silica gel eluted with ethyl acetate). The appropriate fractions were collected and concentrated. The residue was recrystallized from ethyl acetate:hexane to provide 1.47 g (56%) of product, mp 108°–110° C.

| ANALYSIS: | | | |
|---|---|---|---|
| Calculated for $C_{25}H_{26}N_4O$: | 75.35% C | 6.58% H | 14.06% N |
| Found: | 75.39% C | 6.58% H | 14.13% N |

EXAMPLE 22

Z-1-(2-Isoindol-1-ono)-4-[4-(2-pyrimidino)-1-piperazinyl]-2-butene hydrate

Triethylsilane (0.85 g) was added to a solution of Z-1-(3-hydroxy-2-isoindol-1-ono)-4-[4-(2-pyrimidino)-1-piperazinyl[-2-butene (1.79 g), dichloromethane (20 ml) and trifluoroacetic acid (7.5 ml) After 1 hr., the reaction mixture was evaporated and the residue was dissolved in dichloromethane (150 ml). The solution was washed with 2.5% aqueous sodium hydroxide solution, brine, dried over anhydrous sodium sulfate, filtered, and the filtrate was concentrated. Recrystallization of the residue from ethyl acetate:hexane provided 1.56 g (87%) of product, mp 87°–90° C.

| ANALYSIS: | | | |
|---|---|---|---|
| Calculated for $C_{20}H_{23}N_5O \cdot H_2O$: | 65.37% C | 6.86% H | 19.06% N |
| Found: | 65.68% C | 6.92% H | 19.16% N |

EXAMPLE 23

1-(3-Hydroxy-2-isoindol-1-ono)-4-[4-(2-quinolino)-1-piperazinyl]-2-butyne

Sodium borohydride (1.35 g) was added to a suspension of 1-(N-phthalimido)-4-[4-(2-quinolino)-1-piperazinyl]-2-butyne (6.50 g), methanol (200 ml) and dichloromethane (30 ml) at room temperature. After 5 mins, the reaction mixture was evaporated and the residue was purified by column chromatography (75 g silica gel, eluted with ethyl acetate). The appropriate fractions were collected and concentrated. Recrystallization of the residue from ethyl acetate:hexane afforded 5.42 g (83%) of product, mp 163°–165° C.

| ANALYSIS: | | | |
|---|---|---|---|
| Calculated for $C_{25}H_{24}N_4O_2$: | 72.79% C | 5.86% H | 13.58% N |
| Found: | 72.83% C | 5.84% H | 13.45% N |

EXAMPLE 24

Z-1-(3-Hydroxy-2-isoindol-1-ono)-4-[4-(2-pyrimidino)-1-piperazinyl]-2-butene

Sodium borohydride (1.80 g) was added in three portions at room temperature to a solution of Z-1-(N-phthalimido)-4-[4-(2-pyrimidino)-1-piperazinyl]-2-butene (5.80 g), methanol (50 ml) and dichloromethane (20 ml). The reaction mixture was quenched with 2.5% aqueous sodium hydroxide solution and diluted with water (50 ml) and dichloromethane (50 ml). The aqueous phase was washed with two 75 ml-portions of dichloromethane, and the combined organic layers were washed with brine, dried over anhydrous sodium sulfate, filtered, and the filtrate was concentrated. The residue was purified by column chromatography (225 g silica gel, eluted with 3% methanol:ethyl acetate). The appropriate fractions were collected and concentrated to give 4.09 g (70%) of product. Recrystallization from ethyl acetate:hexane produced the analytical sample, mp 119°–121° C.

| ANALYSIS: | | | |
|---|---|---|---|
| Calculated for $C_{20}H_{232}N_5O_2$: | 65.73% C | 6.34% H | 19.17 N |
| Found: | 65.98% C | 6.35% H | 19.40% N |

EXAMPLE 25

E-1-(2-Pyrrolo[3,4-c]pyridine-1,3-dione)-4-[4-(3-trifluoromethylphenyl)-1-piperazinyl]-2-butene A solution of 3,4-pyridinedicarboxylic anhydride (1.75 g), E-1-amino-4-[4-(3-trifluoromethylphenyl)-1-piperazinyl]-2-butene (3.00 g), xylenes (50 ml) and pyridine (12 ml) was heated under reflux. After 22.5 hrs, the reaction mixture was evaporated and the residue was purified by flash chromatography (50 g silica gel, eluted with 40–75% ethyl acetate:dichloromethane). The appropriate fractions were collected and evaporated to give 3.50 g (81%) of product. Recrystallization from hexane gave the analytical sample, mp 103°–105° C.

| ANALYSIS: | | | |
|---|---|---|---|
| Calculated for $C_{22}H_{21}F_3N_4O_2$: | 61.39% C | 4.92% H | 13.02% N |
| Found: | 61.48% C | 4.92% H | 13.00% N |

EXAMPLE 26

E-1-(6-Pyrrolo[3,4-b]pyridine-5,7-dione)-4-[4-(3-trifluoromethylphenyl]-1-piperazinyl]-2-butene A solution of 2,3-pyridinedicarboxylic anhydride (1.75 g), E-1-amino-4-[4-(3-trifluroomethylphenyl)-1-piperazinyl]-2-butene (3.00 g) in xylenes (50 ml) and pyridine (12 ml) was heated under reflux. After 23 hrs, the reaction mixture was evaporated and the residue was purified by flash chromatography (50 g silica gel, eluted with 40–50% ethyl acetate:dichloromethane). The appropriate fractions were collected and concentrated to provide 2.95 (69%) of product. Recrystallization from ether:hexane gave the analytical sample, mp 121°–124° C.

| ANALYSIS: | | | |
|---|---|---|---|
| Calculated for $C_{22}H_{21}F_3N_4O_2$: | 61.39% C | 4.92% H | 13.02% N |
| Found: | 61.29% C | 4.85% H | 12.96% N |

EXAMPLE 27

Z-1-[N-(2-Hydroxymethyl-1-benzamido)]-4-[4-(4-(2-pyrimidino)-1-piperazinyl]-2-butene Sodium borohydride (1.80 g) was added in three portions to a solution of Z-1-(N-phthalimido)-4-[4-(2-pyrimidino)-1-piperazinyl]-2-butene Sodium borohydride (1.80 g) was added in three portions to a solution of Z-1-(N-phthalimido)-4-[4-(2-pyrimidino)-1-piperazinyl]-2-butene (5.80 g) methanol (60 ml) and dichloromethane (20 ml) at room temperature. The reaction mixture was quenched with 2.5% aqueous sodium hydroxide solution (10 ml) and diluted with water (50 ml) and dichloromethane (50 ml). The aqueous phase was washed with two 75 ml-portions of dichloromethane, and the combined organic layers were washed with brine, dried over anhydrous sodium sulfate, filtered, and the filtrate was concentrated. The residue was purified by column chromatography (225 g silica gel, eluted with 3% methanol:ethyl acetate). The appropriate fractions were collected and evaporated. Recrystallization of the residue from ethyl acetate:hexane provide 0.68 g of product, mp 136°–138° C.

| ANALYSIS: | | | |
|---|---|---|---|
| Calculated for $C_{20}H_{25}N_5O_2$: | 65.37% C | 6.86% H | 19.06% N |
| Found: | 65.09% C | 6.91% H | 18.96% N |

EXAMPLE 28

1-Amino-4-[4-(3-trifluoromethylphenyl)-1-piperazinyl]-2-butyne

A biphasic solution of 1-(N-phthalimido)-4-[4-(3-trifluoromethylphenyl-1-piperazinyl]-2-butyne (46.0 g), dichloromethane (700 ml) and 40% aqueous methylamine (127 ml) was stirred at room temperature for 44 hrs. The reaction mixture was diluted with water (500 ml), and the organic phase was separated, washed four times with water (1 l), brine (800 ml), dried over anhydrous sodium sulfate, filtered, and the filtrate was concentrated. Distillation of the residue gave 28.3 g (89%) of product, bp 155°–165° C. (0.05 mm).

| ANALYSIS: | | | |
|---|---|---|---|
| Calculated for $C_{15}H_{18}F_3N_3$: | 60.59% C | 6.10% H | 14.13% N |
| Found: | 60.18% C | 6.16% H | 14.05% N |

EXAMPLE 29

1-Amino-4-[4-(2-methoxyphenyl)-1-piperazinyl]-2-butyne

A biphasic solution of 40% aqueous methylamine (75 ml) 1-(N-phthalimido)-4-[4-(2-methoxyphenyl)-1-piperazinyl]-2-butyne (29.3 g) and dichloromethane (300 ml) was stirred at room temperature for 22 hrs. The aqueous layer was separated. The organic phase was washed with water until the aqueous washings were neutral, brine (500 ml) and 2.5% hydrochloric acid (100 ml), basified with 10% aqueous sodium hydroxide solution, and the mixture was extracted twice with dichloromethane (150 ml). The combined organic phases were washed with water (300 ml), brine (300 ml), dried over anhydrous sodium sulfate, filtered, and the filtrate was concentrated to give 16.8 g (86%) of product, as an oil.

| ANALYSIS: | | | |
|---|---|---|---|
| Calculated for $C_{15}H_{21}N_3O$: | 69.46% C | 8.16% H | 16.20 N |
| Found: | 68.95% C | 8.11% H | 16.04% N |

EXAMPLE 30

E-1-Amino-4-[4-(3-trifluoromethylphenyl)-1-piperazinyl]-2-butene

A solution of 1-amino-4-[4-(3-trifluoromethylphenyl)-1-piperazinyl]-2-butyne (25.8 g) and tetrahydrofuran (40 ml) was added dropwise over 45 mins to a suspension of lithium aluminum hydride (6.05 g) and tetrahydrofuran (500 ml), while the reaction temperature was maintained below 5° C. After the addition was complete, the reaction mixture was stirred at room temperature for 14.5 hrs and at 45° C. for 3.5 hrs. The reaction mixture was cooled to 0° C. and quenched by sequential addition of water (6 ml) 15% aqueous sodium hydroxide solution (6 ml), and water (18 ml). The mixture was filtered through a bed of celite, washed with dichloromethane (200 ml), and the filtrate was concentrated. Purification of the residue by distillation gave 25.0 g (96%) of product, bp 135° C., (0.03 mm).

| ANALYSIS: | | | |
|---|---|---|---|
| Calculated for $C_{15}H_{20}F_3N_3$: | 60.18% C | 6.74% H | 14.04% N |
| Found: | 60.27% C | 6.74% H | 14.05% N |

EXAMPLE 31

E-1-Amino-4-[4-(2-methoxyphenyl)-1-piperazinyl]-2-butene

A solution of 1-amino-4-[4-(2-methoxyphenyl)-1-piperazinyl]-2-butyne (13.4 g) in tetrahydrofuran (150 ml) was added dropwise over 45 mins to a suspension of lithium aluminum hydride (3.91 g) in tetrahydrofuran (500 ml), while the reaction temperature was maintained below 5° C. The reaction mixture was allowed to warm to room temperature and was stirred at room temperature for 20 hrs. Water (3.9 ml), 15% aqueous sodium hydroxide (3.9 ml) and water (12 ml) were added sequentially, while the reaction temperature was kept below 30° C. The precipitate was filtered through a bed of celite, washed three times with diethyl ether (100 ml), filtered, and the filtrate was concentrated. Recrystallization of the residue from hexane gave 7.31 g (54%) of product, mp 63°–67° C.

| ANALYSIS: | | | |
|---|---|---|---|
| Calculated for $C_{15}H_{23}N_3O$: | 68.93% C | 8.87% H | 16.08% N |
| Found: | 68.59% C | 8.81% H | 15.80% N |

EXAMPLE 32

2-(2-Propargyl)-3-hydroxyphthalimidine

Sodium borohydride (1.50 g) was added to a suspension of N-propargylphthalimid (10.0 g) in methanol (150 ml) at room temperature. After 1 hr 2.5% aqueous sodium hydroxide solution (5 ml) was added, and the reaction mixture was evaporated. The residue was purified by flash chromatography (100 g silica gel, eluted with ethyl acetate). The appropriate fractions were collected and evaporated. Recrystallization of the residue from ethyl acetate:hexane provided 7.74 g (77%) of product, mp 150°–153° C.

| ANALYSIS: | | | |
|---|---|---|---|
| Calculated for $C_{11}H_9NO_2$: | 70.57% C | 4.85% H | 7.48% N |
| Found: | 70.36% C | 4.80% H | 7.48% N |

5,334,715
27
28
REACTION SCHEME A
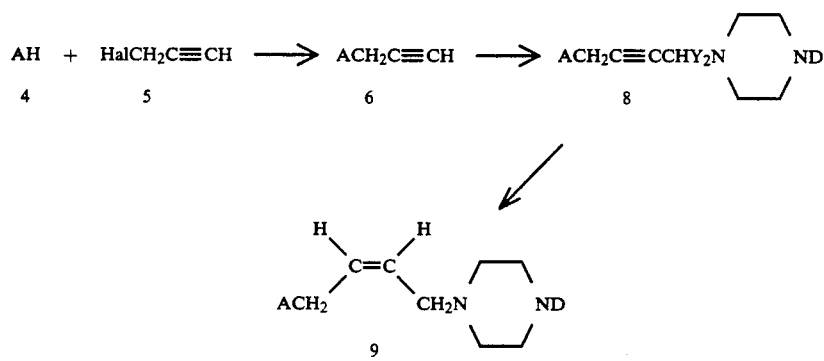
wherein A, D, and Hal are as hereinbeforedescribed
REACTION SCHEME B
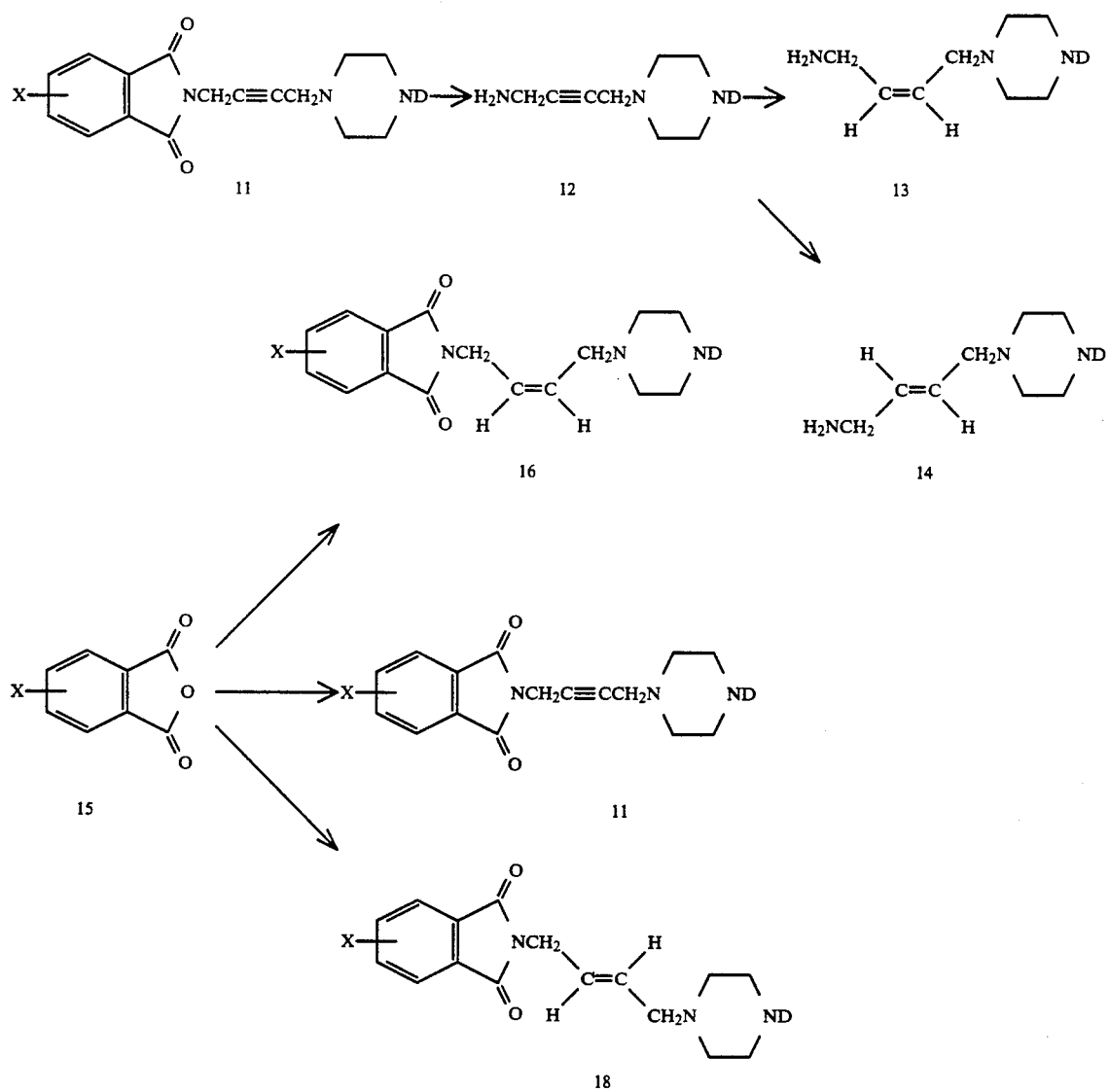
wherein D and X are as hereinbeforedescribed

REACTION SCHEME C

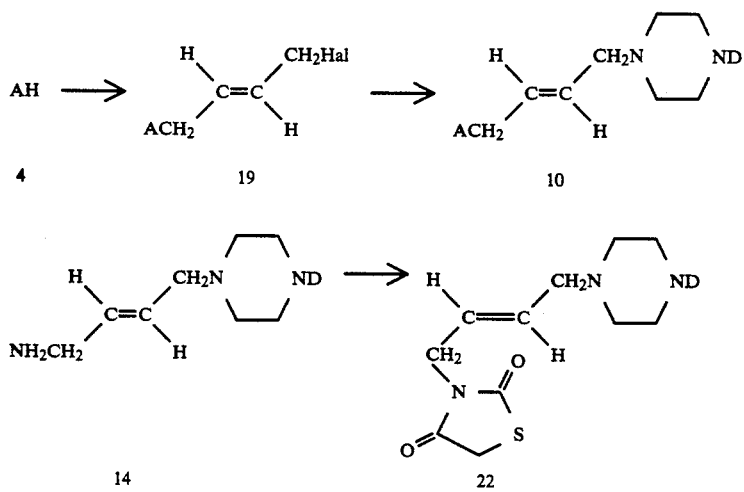

wherein A, D, and Hal are as hereinbeforedescribed

REACTION SCHEME D

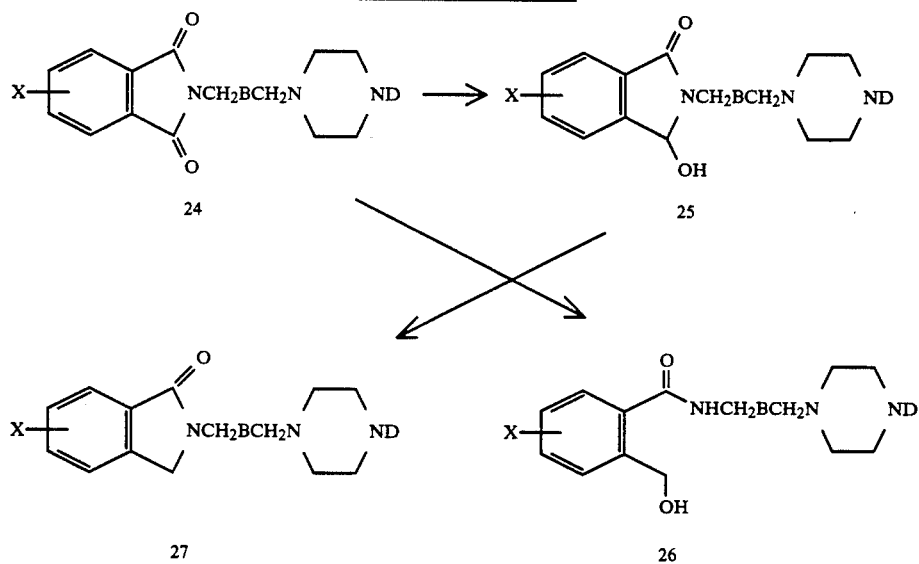

wherein B, D, and X are as hereinbeforedescribed

We claim:
1. A compound of the formula

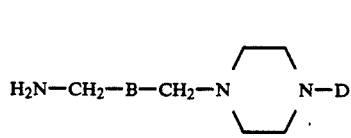

wherein B is a group of the formula

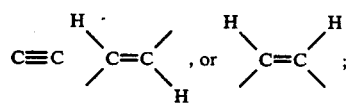

D is a group of the formula

wherein Y is hydrogen, loweralkyl, loweralkoxy, halogen, or trifluoromethyl; a group of the formula

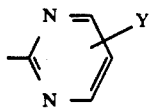

wherein Y is as above; a group of the formula

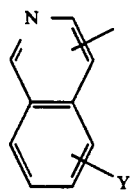

wherein Y is as above; a group of the formula

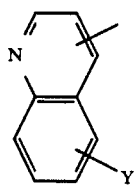

wherein Y is as above; a group of the formula

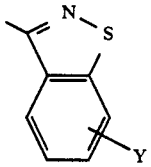

wherein Y is as above; a group of the formula

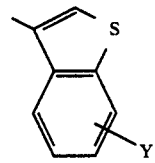

wherein Y is as above; the solid line (—) refers to point of attachment of the group to the indicated member of the formula; the optical isomers; or a pharmaceutically acceptable salts thereof.

2. The compound according to claim 1 wherein D is a group of the formula

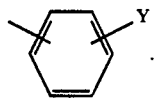

3. The compound according to claim 2 which is 1-amino-4-[4-(3-trifluoromethylphenyl)-1-piperazinyl]-2-butyne.

4. The compound according to claim 2 which is 1-amino-4-[4-(2-methoxyphenyl)-1-piperazinyl]-2-butyne.

5. The compound according to claim 2 which is E-1-amino-4-[4-(3-trifluoromethylphenyl)-1-piperazinyl]-2-butene.

6. The compound according to claim 2 which is E-1-amino-4-[4-(2-methoxyphenyl)-1-piperazinyl]-2-butene.

* * * * *